(12) United States Patent
Kenseth et al.

(10) Patent No.: US 6,833,919 B2
(45) Date of Patent: Dec. 21, 2004

(54) MULTIPLEXED, ABSORBANCE-BASED CAPILLARY ELECTROPHORESIS SYSTEM AND METHOD

(75) Inventors: Jeremy R. Kenseth, Ames, IA (US); Ho-Ming Pang, Ames, IA (US); Roy F. Strasburg, Ames, IA (US)

(73) Assignee: COMBISEP, Ames, IA (US)

( * ) Notice: Subject to any disclaimer, the term of this patent is extended or adjusted under 35 U.S.C. 154(b) by 86 days.

(21) Appl. No.: 10/269,646

(22) Filed: Oct. 11, 2002

(65) Prior Publication Data

US 2004/0070758 A1 Apr. 15, 2004

(51) Int. Cl.[7] .............................................. G01N 21/00
(52) U.S. Cl. ..................................................... 356/344
(58) Field of Search ......................... 356/344, 445–448; 204/452, 603

(56) References Cited

U.S. PATENT DOCUMENTS

| | | | |
|---|---|---|---|
| 4,960,999 A | 10/1990 | McKean et al. | |
| 5,221,448 A | * 6/1993 | Weinberger et al. | ......... 204/452 |
| 5,324,401 A | 6/1994 | Yeung et al. | |
| 5,374,527 A | 12/1994 | Grossman | |
| 5,582,705 A | 12/1996 | Yeung et al. | |
| 5,584,982 A | * 12/1996 | Dovichi et al. | ............. 204/603 |
| 5,667,656 A | * 9/1997 | Kambara | ..................... 204/603 |
| 5,695,626 A | 12/1997 | Yeung et al. | |
| 5,741,411 A | 4/1998 | Yeung et al. | |
| 5,900,934 A | 5/1999 | Gilby et al. | |
| 6,005,663 A | * 12/1999 | Waterhouse et al. | ......... 356/344 |
| 6,120,667 A | * 9/2000 | Hayashizaki et al. | ........ 204/603 |
| 6,352,633 B1 | 3/2002 | Liu et al. | |
| 6,462,816 B1 | 10/2002 | Doolen et al. | |
| 6,531,044 B1 | * 3/2003 | Anazawa et al. | ............ 204/603 |
| 2001/0040094 A1 | * 11/2001 | Inaba et al. | ................ 204/603 |
| 2003/0215882 A1 | * 11/2003 | Grossman et al. | ............ 435/7.1 |

FOREIGN PATENT DOCUMENTS

| | | |
|---|---|---|
| EP | 1 109 014 A2 | 6/2001 |
| WO | WO 00/06996 | 2/2000 |
| WO | PCT - WO 00/30751 | 6/2000 |
| WO | WO 01/18528 A1 | 3/2001 |

OTHER PUBLICATIONS

Jaiqi Wu and Janusz Pawliszyn, Absorption Spectra and Multicapillary Imaging . . . , University of Waterloo, May 1995, 1567–71, vol. 120, Ontario, Canada.

Culbertson and Jorgenson, Lowering the UV Absorbance . . . , University of North Carolina, Jul. 1998, 2629–38, vol.70, No. 13.

* cited by examiner

Primary Examiner—Michael P. Stafira
(74) Attorney, Agent, or Firm—McKee, Voorhees & Sease, P.L.C.

(57) ABSTRACT

A multiplexed, absorbance-based electrophoresis system for analyzing multiple samples simultaneously without use of a mask or slit comprising a light source, a planar array of capillary tubes and a detector positioned off-axis with the light source and positioned on-axis with and parallel to the planar array of capillary tubes. Other embodiments include vacuum use attached to the capillary tubes to increase the speed of detection.

59 Claims, 8 Drawing Sheets

MULTIPLEXED, ABSORBANCE-BASED CAPILLARY ELECTROPHORESIS SYSTEM AND METHOD

TECHNICAL FIELD OF THE INVENTION

This invention relates to a multiplexed, absorbance-based capillary electrophoresis system and to a method of using it.

BACKGROUND OF THE INVENTION

The rapid development of biological and pharmaceutical technology has posed a challenge for high-throughput analytical methods. For example, current development of combinatorial chemistry has made it possible to synthesize hundreds or even thousands of compounds per day in one batch. Characterization and analysis of such huge numbers of compounds has created a bottleneck. Parallel processing (i.e., simultaneous multi-sample analysis) is a natural way to increase the throughput. However, due to limitations related to column size, pressure requirements, detector and stationary phase materials, it is very difficult to build a highly multiplexed high-performance liquid chromatography (HPLC) system. The same goes for building a highly multiplexed gas chromatography (GC) system.

High performance capillary electrophoresis (CE) has rapidly become an important analytical tool for the separation of a large variety of compounds ranging from small inorganic ions to large biological molecules. To perform a conventional separation, a capillary tube is filled with a buffer solution, a sample is loaded into one end of the capillary tube, both ends of the capillary tube are immersed in the buffer solution and a large potential is applied across the capillary tube. The sample components are separated electrophoretically as they migrate through the capillary tube.

CE is used for general separations, enantiomeric separations, the peptide mapping of proteins, amino acid analysis, nucleic acid fractionation and the quantitative measurement of acid dissociation constants ($pK_a$ values) and octanol-water partition coefficients (log $P_{ow}$ values). What all these applications have in common is the measurement of the mobility of chemical species in a capillary tube.

With attractive features such as rapid analysis time, high separation efficiency, small sample size, and low solvent consumption, CE is increasingly used as an alternative or complimentary technique to HPLC. For example, the use of capillary gel electrophoresis has greatly improved DNA sequencing rates compared to conventional slab gel electrophoresis. Part of the improvement in speed, however, has been offset by the inability to accomodate multiple lanes in a single run that is inherent in slab gels. Highly multiplexed capillary electrophoresis, by making possible hundreds or even thousands of parallel sequencing runs, represents an attractive approach to overcome the current throughput limitations of existing DNA sequencing instrumentation. Such a system has been disclosed in U.S. Pat. Nos. 5,582,705 (Yeung et al.), 5,695,626 (Yeung et al.) and 5,741,411 (Yeung et al.). In this system, a fluorescent sample is separated by electrophoresis inside a capillary tube. A laser irradiates one section of the capillary tube. When the sample component migrates through the irradiated portion of the tube, the fluorescence emission is detected by an optical detector.

While fluorescence detection is suitable for DNA sequencing applications because of its high sensitivity and special labeling protocols, many samples of interest do not fluoresce. UV absorption detection is useful because of its ease of implementation and wider applicability, especially for the deep-UV (200–220 nm) detection of organic and biologically important compounds. In a UV detection system, a section of capillary tube is irradiated with a UV light source. A photodetector detects the light that passes through the tube. When a UV absorbing sample component passes through the irradiated portion of the capillary tube, the photodetector detects less passed light (indicating absorbance). In this way an electropherogram, a plot of absorbance versus time, can be produced.

A capillary isoelectric focusing system using a two-dimensional charge-coupled device (CCD) detector, in which one dimension represents the capillary length and the other dimension records the absorbance spectrum, has been described by Wu and Pawliszyn, Analyst (Cambridge), 120, 1567–1571 (1995). The system has been used with two capillary tubes, but is not easily adapted for three or more capillary tubes because the system requires the capillary tubes to be separated by space. Instead of providing wavelength resolution in the second CCD dimension, isoelectric focusing in two capillary tubes is simultaneously monitored. The use of optical fibers for illumination, however, has led to low light intensities and poor UV transmission. So, only visible wavelengths have been employed for the detection of certain proteins. Because the CCD has a very small electron well capacity (about 0.3 million electrons), the limit of detection (LOD) of this system is limited by the high shot noise in absorption detection. The use of the CCD produces an overwhelming amount of data per exposure, limiting the data rate to one frame every 15 seconds. Also, the imaging scan utilized is not suitable for densely packed capillary arrays because of the presence of mechanical slits to restrict the light paths. Further, in order to avoid cross-talk, only square capillary tubes can be used.

Photodiode arrays (PDA) are used in many commercial CE and HPLC systems for providing absorption spectra of the analytes in real time. Transmitted light from a single point in a flow stream is dispersed by a grating and recorded across a linear array. A capillary zone electrophoresis system using a photodiode array as an imaging absorption detector has been described by Culbertson and Jorgenson, Anal. Chem., 70, 2629–2638 (1998). Different elements in the array are used to image different axial locations in one capillary tube to follow the progress of the separation. Because the PDA has a much larger electron well capacity (tens of millions of electrons), it is superior to the CCD for absorption detection. Time-correlated integration is applied to improve the signal-to-noise ratio (S/N).

Gilby described an absorption detection approach for the simultaneous analysis of multiple systems in U.S. Pat. No. 5,900,934. This system includes a photodetector array comprising a plurality of photosensitive elements connected to provide a serial output. The elements are typically pixels of a photodiode array (PDA). The elements are illuminated by a light source positioned to illuminate at least a portion of the photodetector array. The light source may be an AC or DC mercury lamp or other useable light source for chromatography. An array of separation channels is disclosed between the light source and the photodetector array, each of the separation channels having a lumen, a sample introduction end and a detection region disposed opposite the sample introduction end. The array is a multiple parallel capillary electrophoresis system. A mask element having at least one aperture for each associated separation channel is required. Each aperture corresponds to its associated separation channel, thereby selectively permitting light from the light source to pass through the lumen of its associated separation channel. At least a portion of the light passing through the lumen of the associated separation channel falls on the respective photo sensitive element of the photo detector array to effect measurement of absorption of light by a sample introduced into the sample introduction end of the associated separation channel.

The system described by Gilby et al. has disadvantages because it limits the amount of light impinging on the separation channel, providing less than desirable light intensity to the PDA. Further, aligning the apertures and the mask elements with the separation channels, e.g., capillary tubes, is difficult for several reasons. For example, positioning the capillary tubes with equal separation there between is difficult as the capillary tubes are generally not of equal dimension, e.g., diameter tolerances very greatly. Further, for example, the mask geometry does not provide identical light paths, which leads to non-linear response. Also, a mask can produce stray light, which leads to poor detection limits, and does not completely eliminate cross-talk from the adjacent capillary tubes, since the light beams are diverging and cannot escape the detector element. In addition, a mask can be difficult to manufacture, due to the requirement of uniformity. Also, Gilby places the sample and the PDA too close together, resulting in stray light, cross-talk and the inability to use the maximum path length of light.

Yeung et al., in PCT Application WO 01/18528A1, disclosed a multiplexed, absorbance-based capillary electrophoresis system for analyzing multiple samples simultaneously, without use of a mask or slit, comprising a light source, a planar array of capillary tubes and a detector positioned on-axis with the light source and positioned on-axis with and parallel to the planar array of capillary tubes at a distance of at least about 10 times a cross-sectional distance of a capillary tube measured orthogonally to the planar array of multiple capillary tubes.

The system described by Yeung et al. works, but has disadvantages. In Yeung's system, the detector is positioned on-axis with the light source. Therefore, light that passes between the capillary tubes and light that passes through the capillary tubes (and samples) both strike the detector. The light that passes between the capillary tubes is not of interest since it represents a measurement of nothing, but provides a peak that is registered by the detector and recorded by the associated software. It is preferable that light that passes between the capillary tubes never reaches the detector.

In addition, the rate of sample migration in the system described by Yeung et al. is slower than ideal, especially when performing some types of separations employing high current generating buffers. This is due to the fact that the high currents generated by some buffers lead to excessive joule heating in the capillary array, which can degrade the quality and reproducibility of the separation. In such situations it is necessary to lower the operating voltage, resulting in increased analysis times. An approach is therefore desired in these situations to improve the analysis time.

Some applications described by Yeung et al. using Yeung's system, while novel, are limited due to the fact that all separations utilize the same buffer for the outlet and the inlet reservoirs. While Yeung has simultaneously performed separations using different buffers in different capillary tubes of an array, the outlet ends of the capillary tubes were bundled separately and separate buffer reservoirs were used for each different buffer. This approach also required the filling of the different capillary bundles individually by hand with a syringe which is not practical from an automation or ease of use standpoint.

In summary, while other multiplexed, absorbance-based capillary electrophoresis systems exist, there is a need for a system without a mask or slit designed such that the majority of light that passes between capillary tubes in the planar array of capillary tubes does not reach the detector, such that separations can be performed at a faster rate, and, finally, so that different buffers can be examined in different capillary tubes simultaneously and in an automated fashion.

The primary objective of this invention is to fulfill the above described needs with an improved multiplexed, absorbance-based capillary electrophoresis system.

These and other objects, features and/or advantages of the present invention will become apparent from the specification and claims.

SUMMARY OF THE INVENTION

The present invention is a multiplexed, absorbance-based capillary electrophoresis system. Specifically, the invention is an improvement on the system disclosed by Yeung et al. in PCT Application WO 01/18528A1, published Mar. 15, 2001, herein incorporated by reference in its entirety. The improvements are three-fold. First, the light source is not on-axis with the detector. This ensures that the great majority of the light that actually hits the detector passed through the capillary tube containing the sample. Second, the rate of sample migration through the capillary tubes is increased by applying a vacuum to the exit end of the tubes. Thus, speed and data processing are enhanced. Third, a single, common outlet reservoir is used in conjunction with different inlet reservoirs. This offers the ability to simultaneously evaluate different buffer conditions in different capillary tubes of the capillary array by filling the capillary tubes from the different inlet reservoirs electrokinetically or with vacuum.

DETAILED DESCRIPTION OF A PREFERRED EMBODIMENT OF THE INVENTION

The invention, as hereinbefore explained, is a multiplexed, absorbance-based capillary electrophoresis system. The invention system and method are for the separation, detection and identification of chemical species.

Figure 1:
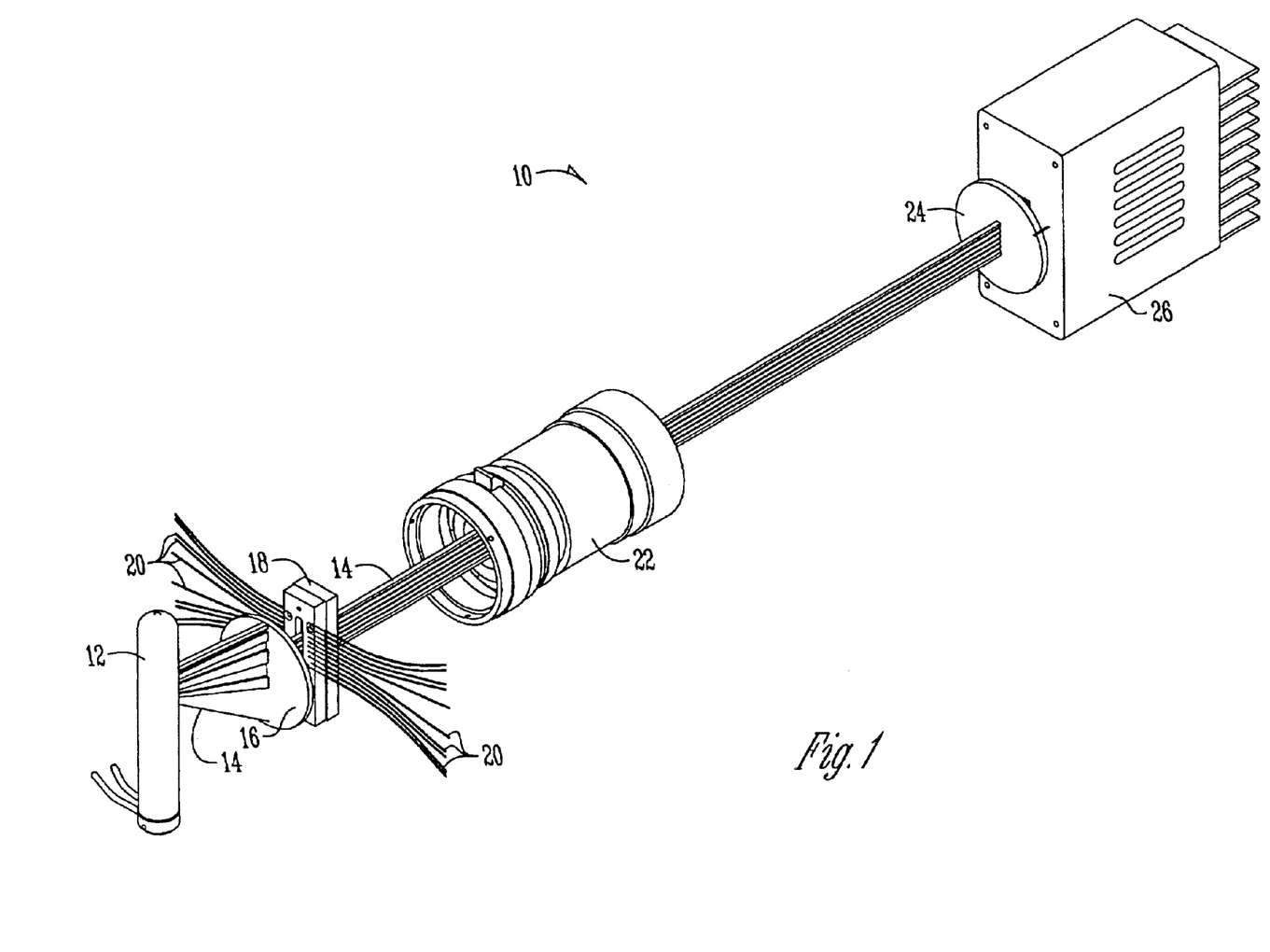
FIG. 1 presents a schematic diagram of the absorbance-based capillary electrophoresis system.

Referring to FIG. 1, 10 designates the absorbance-based capillary electrophoresis system. The light beam 14 originates in the light source 12 and then travels through the collimating lens 16, the planar array of capillary tubes 20, the flat-field lens 22, the optical filter 24 and is collected in the detector 26. The array block 18 holds the capillary tubes 20 in place.

The distance between the area where light is emitted from the light source 12 and the planar array of capillary tubes 20 is not critical to the practice of the present invention. However, the shorter the distance between the area where light is emitted from the light source 12 and the planar array of capillary tubes 20, the more light is received by the planar array of capillary tubes 20. The more light that the planar array of capillary tubes 20 receives, the more sensitive is the detection. The greater the distance between the area where light is emitted from the light source 12 and the planar array of capillary tubes 20, the more uniform is the light received by the planar array of capillary tubes 20.

Preferably, the distance between the planar array of capillary tubes 20 and the detector 26 is at least about 10 times, more preferably, at least about 100 times, a cross sectional distance of a capillary tube 20 measured orthogonally to the plane of the planar array of capillary tubes 20. The critical feature is that the distance must be such that the entire array is visible and in focus. Thus, the distance between the planar array of capillary tubes 20 and the detector 26 is preferably from about 1 centimeter to about 100 centimeters, more preferably from about 3 centimeters to about 40 centimeters, and most preferably from about 20 centimeters to about 40 centimeters.

Figure 2A:
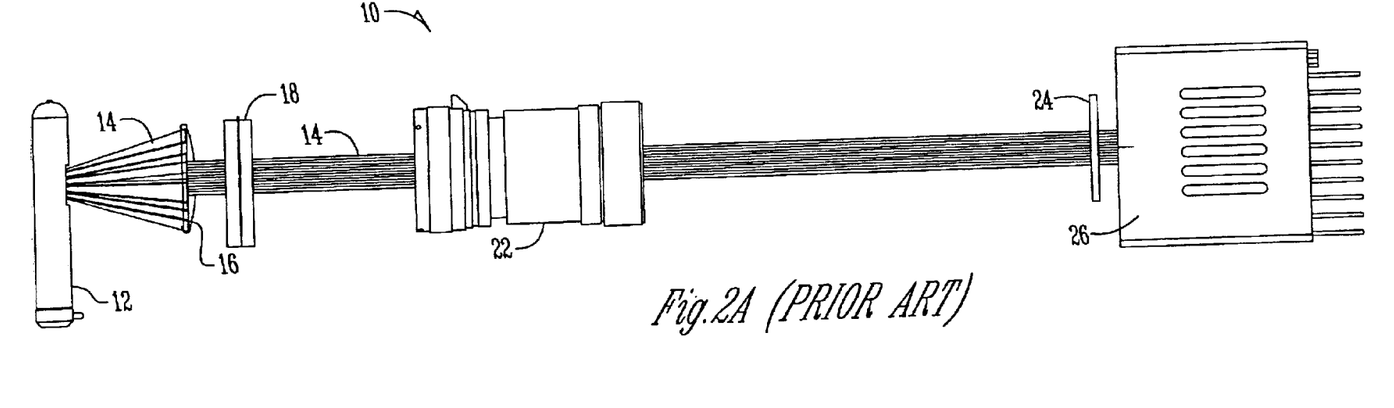
FIG. 2A presents a schematic diagram of a light source positioned on-axis with a detector.
Figure 2B:
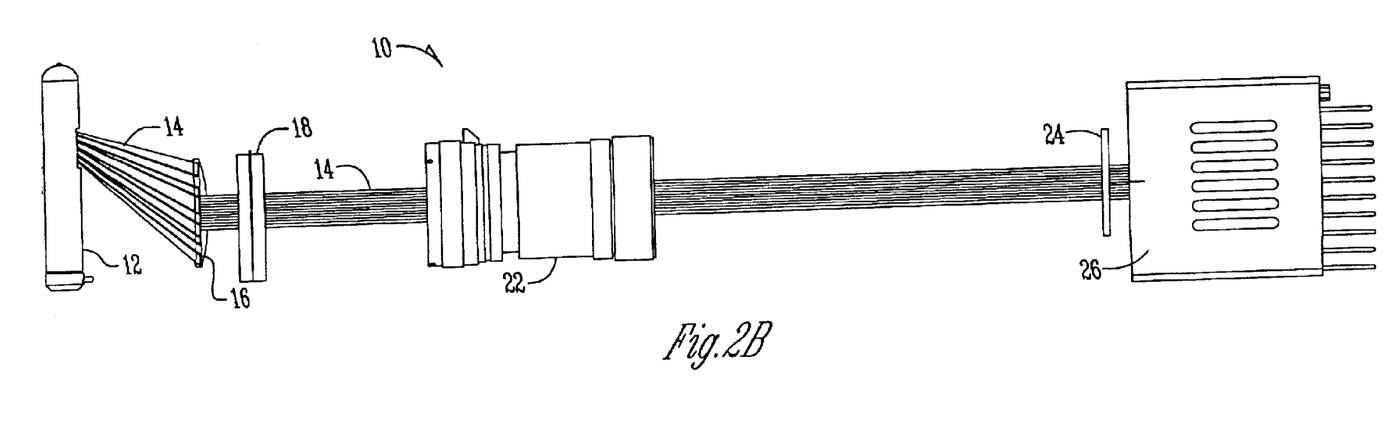
FIG. 2B presents a schematic diagram of a light source positioned off-axis with a detector all in accord with the invention.

The invention is distinguished from the invention of Yeung et al. (PCT Application WO 01/18528A1) in that the area where light is emitted from the light source 12 is positioned off-axis, rather than on-axis, with the detector 26. FIG. 2A shows the prior art (Yeung et al.) where the area where light is emitted from the light source 12 is positioned on-axis with the detector 26. FIG. 2B shows the area where light is emitted from the light source 12 positioned off-axis with the detector 26. When utilizing an on-axis alignment, the area where light is emitted from the light source 12, collimating lens 16, planar array of capillary tubes 20, flat-field lens 22 and detector 26 all lie on a common axis. In this arrangement, light originating from the light source 12 will predominately pass either directly through the capillary tubes 20 of the array, between the capillary tubes 20, or be refracted and absorbed by the walls of the capillary tubes 20. The resulting pattern observed on the (linear photodiode array) detector 26 (FIG. 4A) is comprised of high intensity peaks from the light passing between the capillary tubes 20 and lower intensity peaks originating from light passing directly through the capillary tubes 20 (the desired signal). These two types of peaks are separated by minima corresponding to the capillary tube 20 walls.

In an off-axis alignment, the area where light is emitted from the light source 12 is moved slightly off-axis from the other optical components. A significant consequence of moving the light source 12 is that the signal on the detector 26 from light passing between the capillary tubes 20 of the array is strongly diminished (FIG. 4B). As a result, only light passing through the capillary tubes 20 is significantly observed by the detector 26.

The angle formed by the middle of the flat-field lens 22, the middle of the collimating lens 16 and the center of the area where light is emitted from the light source 12 is defined here as the offset angle. In an on-axis alignment, for example, the offset angle is 180°. In an off-axis alignment, the offset angle is less than 180° and greater than 135°. Preferably, the offset angle is less than 180° and greater than 160°.

When performing simultaneous detection of the different capillary tubes 20 of the array with the detector 26, the off-axis light source 12 alignment is greatly superior to the on-axis arrangement. This is due to the fact that the only appreciable signal observed on the detector 26 using the off-axis arrangement is light passing directly through the respective capillary tubes 20. Therefore, automated selection and assignment of individual pixels to the various capillary tubes 20 of the array is feasible.

In contrast, when using the on-axis arrangement, light passing between the capillary tubes 20 is additionally observed on the detector 26. In this situation, light passing between capillary tubes 20 of the array could be mistaken for light passing directly through a capillary tube 20 of the array, complicating the use of automated capillary tube 20 assignment to different pixels of the detector 26.

The invention is further distinguished from the invention of Yeung et al. in that the outlet ends of the capillary tubes 20 are immersed in a buffer solution and operatively connected to a vacuum source, such as a pump, rather than solely immersed in a buffer solution. By applying vacuum in addition to voltage during a separation, the analysis time can be significantly reduced as compared to using only voltage to impart a separation. As demonstrated in Examples 2 and 3, vacuum assistance greatly decreases the migration times of samples through the capillary tubes 20.

Figure 3:
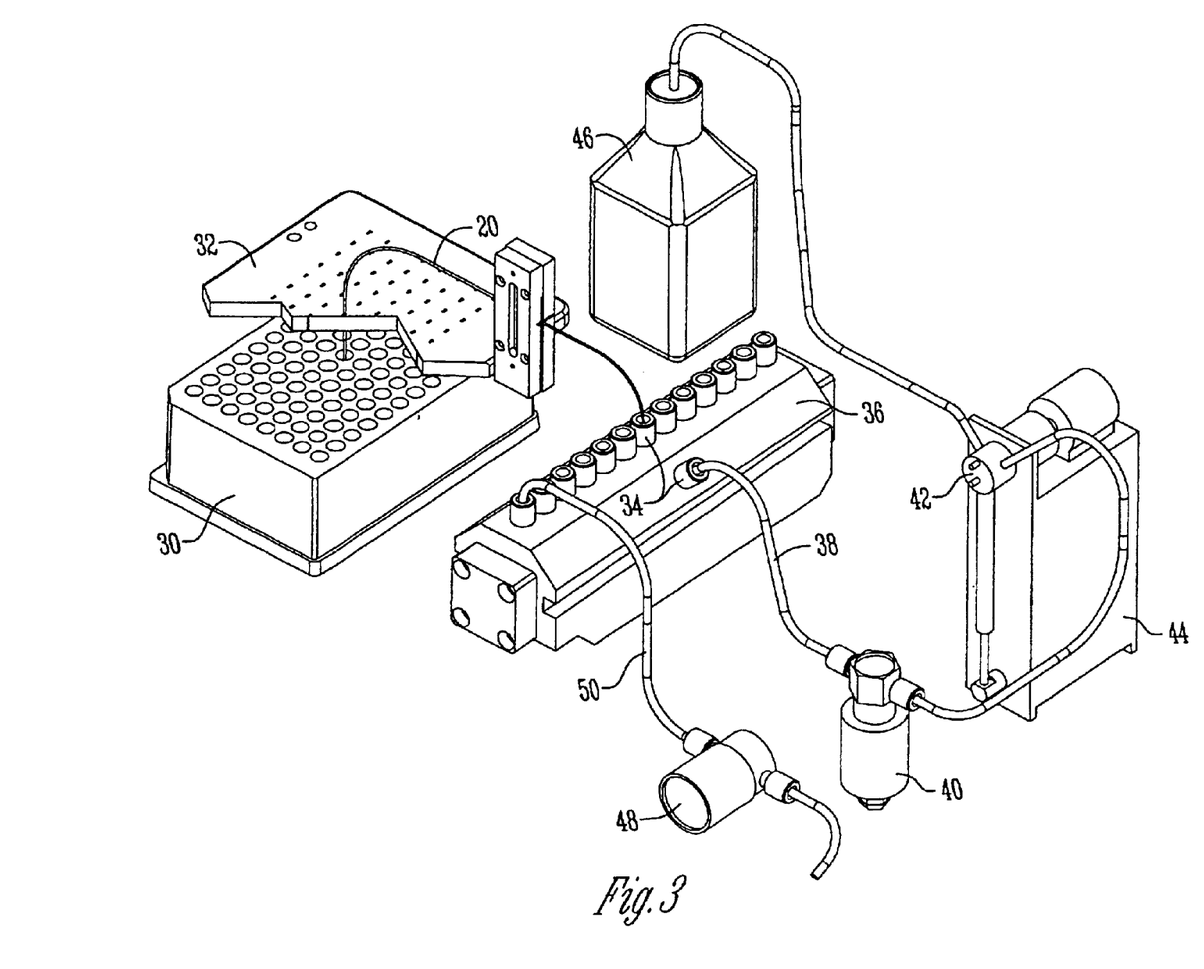
FIG. 3 presents a schematic diagram of the components comprising the vacuum assistance system of the invention.

FIG. 3 illustrates a preferred set-up for vacuum mediated capillary electrophoresis. Only one capillary tube 20 is shown for clarity. The inlet end of the capillary tube 20 is immersed in a buffer solution in an inlet buffer tray 30. The inlet buffer tray may consist of from 1 to 96 separate reservoirs, which mate with the capillary tubes 20 of the array. Above the inlet buffer tray 30, the capillary tube 20 is supported by a circuit board 32. The circuit board 32 is also where an electrical connection is made to the capillary tube 20. The capillary tube 20 next passes through the array block 18 and then into a fitting 34 connected to a reservoir manifold 36. The outlet ends of the capillary tubes 20 are fastened to the reservoir manifold 36 in a manner that creates an airtight seal so that pressure or vacuum can be applied to the capillary tubes 20 and so that the capillary tube 20 ends make contact with the outlet buffer solution in the reservoir manifold 36. Inside the reservoir manifold 36, a second electrical connection is made to the capillary tube 20 and all the capillary tubes 20 are combined into one outlet tube 38 that exits the reservoir manifold 36 through another fitting 34. The outlet tube 38 passes through a pressure transducer 40 and then feeds into a multiport valve 42 connected to a vacuum pump 44. The multiport valve 42 is not essential here. The vacuum pump 44 can connect to the reservoir manifold 36 directly. The multiport valve 42 is used for buffer solution selection only. The vacuum pump preferably provides a small level of vacuum. Examples of suitable vacuum pumps include syringe pumps or diaphragm pumps. A syringe pump is preferred because the syringe plunger movement speed and distance can be concisely computer controlled. When the syringe plunger is pulled a small distance, a small level of vacuum is created. The outlet tube 38 then continues from the multiport valve 42 and terminates at a waste container 46. The vent tube 50 connects a vent valve 48 to the reservoir manifold 36. In operation, buffer solution is continually pumped from the inlet buffer tray 30 through the system to the syringe until it is full and then into the waste container 46 while the vent valve 48 is at closed position. The output signal from the pressure transducer 40 is monitored by a computer so that the vacuum level is continuously monitored. When the vacuum level exceeds the preset level, e.g. −0.1 psi, the computer turns off the vacuum pump. However, when the vacuum level falls below the preset level due to solution movement from the capillary tubes 20 into the reservoir manifold 36, the computer turns on the vacuum pump to maintain the appropriate vacuum level. Therefore a constant vacuum level to the reservoir manifold 36 is maintained during the entire separation period. All capillary tubes 20 that connect to the reservoir manifold 36 will face the same vacuum level. The vacuum level is preferred to be from −0.01 to −2 psi. Too high of vacuum levels will move the samples to the detection windows of the capillary tubes 20 too quickly to obtain reasonable separation.

Another novel feature of the proposed invention is that a different buffer can be used in each capillary tube 20 and its associated inlet reservoir (for example, up to 96 different running buffers if 96 capillary tubes and 96 separate inlet reservoirs are used), with a single, common outlet reservoir manifold 36. The outlet reservoir manifold 36 is initially filled with a common buffer or water. The individual capillary tubes 20 can then be filled from the inlet side with buffer either electrophoretically or by applying vacuum. Using different buffers in different capillary tubes 20 in conjunction with a common reservoir manifold 36 can result in a substantial decrease in reagent costs as expensive buffer additives need only be added to the inlet buffer tray 30. This is the first time that this approach has been successfully employed to simultaneously perform separations using different buffers in different capillary tubes 20 of the array. This approach is particularly useful for substantially accelerating the development of a CE method (Example 4), as most often the running buffer conditions must be optimized for any separation by varying the pH, ionic strength, buffer salts and the use of other additives to achieve a satisfactory separation. In addition, the rapid selection of optimal chiral selector additives (Example 5) and the determination of $pK_a$ values (Example 2) substantially benefit from this approach.

The reservoir manifold 36 is preferably made of an inert material such as polytetrafluoroethylene, polyethylene, polypropylene or polyethylene terephthalate.

By "capillary tubes" 20 is meant at least 3 or more, preferably at least about 10, more preferably at least about 90, and desirably as many as can be accommodated by the system described herein. The capillary tubes 20 allow the passage of light from the light source 12 through the walls of the capillary tubes 20 facing the light source 12, through the samples in the capillary tubes 20, and through the walls of the capillary 20 tubes facing the detector 26. Thus, the walls of the capillary tubes 20 are desirably transparent, although, in some instances, the walls of the capillary tubes 20 can be translucent. It is not necessary for the entirety of the walls of the capillary tubes 20 to allow the passage of light from the light source 12 as described above as long as at least a portion of walls of the tubes allow the passage of light from the light source 12 such that the samples in the capillary tubes 20 are irradiated and light that is not absorbed by the absorbing species and the samples is detectable by the detector 26.

In general, the capillary tubes 20 should have smooth surfaces and uniformly thick walls and be made of a material transparent over the range of wavelengths of light absorbed by an absorbing species in the sample, the absorbance of which is to be detected or measured. Preferred materials for capillary tubes 20 include, but are not limited to, plastics, quartz, fused silica and glass. The cross-section of a capillary tube 20 is not critical to the present invention. However, the smaller the cross-section of the capillary tube 20, the more useful is the capillary tube 20 in highly multiplexed applications as a greater number of capillary tubes 20 can be used in a smaller amount of space. Similarly, the thickness of a walls of the capillary tubes 20 is not critical to the present invention. The walls should be of sufficient thickness as to maintain the structural integrity of the capillary tube 20, yet not so thick as to adversely impede the passage of light through the capillary tube 20. The shape of the capillary tube 20 also is not critical to the present invention. The capillary tube 20 can have any suitable shape. However, the preferred size and shape of the capillary is 150 μm outside diameter, 75 μm inside diameter and circular in shape. Desirably, the shape of the capillary tube 20 is conducive to being closely packed and minimizes the generation of stray light by the container. The capillary tubes 20 are preferably from about 10 cm to about 200 cm long.

Capillary tubes 20 are commercially available by a number of sources including Polymicro Technologies, Inc., Phoenix, Ariz. The capillary tube 20 is preferably coated with a polymer such as polyimide so that it is mechanically stable. The coating must be removed in the region to be irradiated by the light source 12. An excimer laser can be used to remove the polymer coating.

Preferably, the capillary tubes 20 in the planar array are arranged substantially parallel and adjacent to each other. Adjacent capillary tubes 20 can be physically touching each other along all or a portion of their lengths, although slight inconsistencies in capillary wall diameter or other features of the array can prevent them from being in contact along their entire lengths. The planar array of capillary tubes 20 desirably is rigidly mounted to reduce flicker noise.

The electrical potential used for electrophoretic separation is not critical to the invention. A typical potential ranges from 5,000 to 30,000 V.

If a large amount of heat is generated during the method, particularly in the vicinity of the planar array of capillary tubes 20, cooling should be employed to dissipate the heat. Excessive heat can lead to mechanical vibrations between adjacent capillary tubes 20, which, in turn, can lead to excess noise. Fans can cool the capillary tubes 20.

The detector 26 can comprise any suitable means of detecting absorption. Preferably, the detector 26 comprises a plurality of absorption detection elements, such as a plurality of photosensitive elements, which desirably are positioned in a linear array, although a two-dimensional image array detector can be used. Desirably, the detector 26 is parallel to and in-line with a linear array of capillary tubes 20. The detector 26 is desirably rigidly mounted to reduce flicker noise.

Preferably, the detector 26 is a linear photodiode array (PDA). Desirably, the PDA incorporates a linear image sensor chip, a driver/amplifier circuit and a temperature controller, which desirably thermoelectrically cools the sensor chip to a temperature from about 0° C. to about −40° C. Lowering the temperature lowers the dark count and minimizes the temperature drift, thus enabling reliable measurements to be made over a wide dynamic range. The driver/amplifier circuit is desirably interfaced to a computer via an I/O board, which preferably also serves as a pulse generator to provide a master clock pulse and a master start pulse, which are required by the linear image sensor. The PDA records the image linearly, not two-dimensionally. Preferably, the data acquired is written directly to the hard disk in real time. Also, preferably, the signals from up to at least 10 elements of the PDA are displayed in real time.

Preferably, the PDA comprises linearly aligned pixels, in which case each capillary tube is optically coupled to less than about 10 pixels, more preferably from about 7 to about 9 pixels, some of which are coupled to the walls of the capillary and at least one of which is coupled to the lumen of the capillary. A pixel exposed to light produces an electronic signal that is proportional to the intensity of incident light.

The light source 12 preferably emits light of a wavelength in the range from about 180 nm to about 1500 nm. Examples of a suitable light source 12 include mercury (for ultra violet (UV) light absorption), tungsten (for visible light absorption), iodine (for UV light absorption), zinc (for UV light absorption) cadmium (for UV light absorption), xenon (for UV light absorption) or deuterium (for visible light absorption) lamps. Desirably, the light source 12 emits a wavelength of light that will be absorbed by the species of interest. Which wavelength of light is absorbed by the species of interest can be determined using a standard absorption spectrometer. Alternatively, spectroscopic tables that provide such information are available in the art, such as through the National Institute of Science and Technology. Desirably, a maximally absorbed wavelength of light is selected for a given species to be detected or measured such that smaller amounts of the absorbing species can be detected. The light source 12 can be a point source. Also, preferably, the light source 12 has a power output of about 0.5 mW to about 50 mW.

An optical filter 24 is desirably positioned between the planar array of capillary tubes 20 and the detector 26. The optical filter 24 prevents stray light from the outside environment from reaching the detector 26. The filter 24 passes light at and near the wavelength emitted from the light source 12 and blocks light of other wavelengths.

A flat-field lens 22 is desirably positioned between the planar array of capillary tubes 20 and the detector 26. The flat-field lens 22 couples light that is not absorbed by the one or more absorbing species in each sample with the detector 26. While a lens that is not a flat-field lens can be used in the context of the present invention, it is disadvantageous in as much as it does not image the entire field evenly. Consequently, the edges of the field are distorted and the absorption of the capillary tubes 20 positioned at the edges of the field of the lens cannot be detected or measured. The flat-field lens 22 inverts the image of the planar array onto the face of the detector 26.

A collimating lens 16 is desirably positioned between the light source 12 and the planar array of capillary tubes 20. The collimating lens 16 focuses the light from the light source 12 to irradiate the capillary tubes 20 more effectively.

While the sample can be introduced into each capillary tube 20 in a planar array of multiple capillary tubes 20 by any suitable method, preferably the samples are introduced into the capillary tubes 20 by pressure, gravity, vacuum, capillary or electrophoretic action.

The above components are placed to eliminate substantially, and desirably, completely, stray light. There are two kinds of stray light. One kind of stray light is the glare that results from the capillary tubes 20 having sidewalls and interior lumens. The other kind of stray light is that which is due to the presence of other capillary tubes 20. This kind of stray light is referred to as "cross talk." Cross talk essentially is the glare from other capillary tubes 20. Thus, there needs to be sufficient distance between the sample and the flat-field lens 22 to eliminate substantially and, desirably completely the two kinds of glare. The rate of decrease of stray light as the distance increases will eliminate most of the glare from the containers. Glare can be assessed by measuring a totally absorbing material in a container. If there is any light detected, that light is due to glare.

Preferably, raw data sets are extracted into single-diode electropherograms and analyzed by converting the transmitted light intensities collected at the detector 26 to absorbance values using a capillary tube 20 containing only buffer solution as a continuous blank reference (control). Alternatively, as many as five and preferably three adjacent diodes may be summed for each capillary tube 20 of the array to increase the overall light intensity. Root-mean-squared noise in the electropherograms is obtained using a section of baseline near one of the analyte peaks. Mathematical smoothing can be used to reduce noise significantly, without distorting the signal. In this regard, as high a data acquisition rate as possible should be employed to provide more data points for smoothing. Various algorithms including binomial, boxcar and Savitzky-Golay smoothings are preferred methods of mathematical smoothing.

The following examples are offered to illustrate but not limit the invention.

EXAMPLE 1

(Comparison of Detector Output With the Light Source Positioned On-Axis and Off-Axis With the Detector)

Figure 4A:
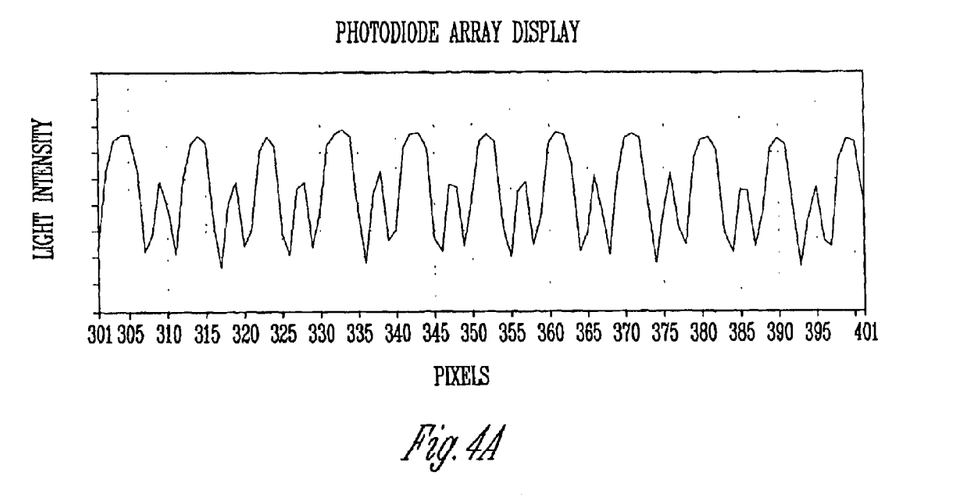
FIG. 4A presents the detector output with the light source on-axis with the detector for comparison purposes.
Figure 4B:
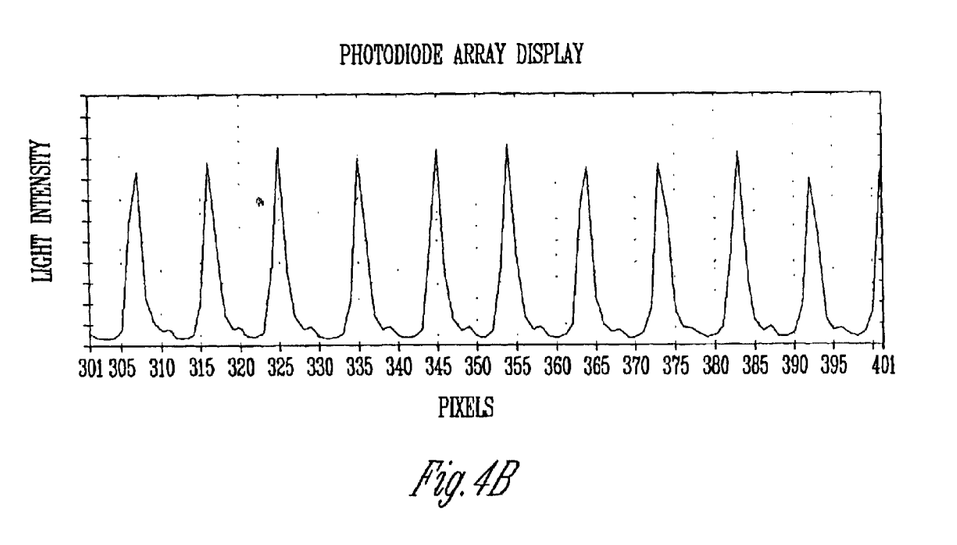
FIG. 4B presents the detector output with the light source off-axis with the detector in accord with the invention.

FIG. 4A presents the detector output with the light source positioned on-axis with the detector. The x-axis represents individual photodiodes of the PDA (1 pixel=1 photodiode). The y-axis represents measured light intensity. Ten capillary tubes are observed within the selected 100-pixel window. The highest intensity, rounded peaks correspond to light passing through the gaps between the capillary tubes, while the less intense peaks correspond to light passing through the capillary tubes. The minimum points (valleys) correspond to light passing through capillary walls.

FIG. 4B presents the detector output with the light source positioned off-axis with the detector. The x-axis represents individual photodiodes of the PDA (1 pixel=1 photodiode). The y-axis represents measured light intensity. Eleven capillary tubes are observed within the selected 100-pixel window. With this alignment, each intense peak corresponds to light passing through a single capillary of the array. The light passing between the capillary tubes has been reduced to a minimum. With this alignment, it is significantly easier, especially for software programs, to identify peaks corresponding to light passing through capillary tubes because there are not also large peaks corresponding to light passing between capillary tubes to choose from.

EXAMPLE 2

(Comparison of Migration Times and $pK_a$ Analysis of Benzoic Acid With and Without Vacuum Assistance)

The $pK_a$ value of a drug compound is of fundamental importance in drug discovery. The $pK_a$ value is defined as the pH at which an ionizable chemical functionality of a compound is 50% ionized, and is an important physicochemical characteristic of a molecule, influencing its solubility, association, complexation, and biological activity. As with log $P_{ow}$ values, it is highly desirable to screen drug compounds early in the development process for their $pK_a$ value. A recently introduced spectroscopic method using multiwavelength UV spectroscopy and a linear pH gradient from pH 2-12 (Tan et al. to 300 compounds per day, but suffers from the inability to discriminate the sample impurities often present in early drug discovery, and requires the different ionization states of a molecule to possess different spectral characteristics, a property not always fulfilled. Conversely, as CE is a separation method, impurities can be resolved from the desired compound, and spectral differences are not required of the molecule because in CE only the electrophoretic mobility of a compound as a function of pH is measured.

Current methods for screening $pK_a$ values by CE use single capillary approaches, and, even with the addition of pressure to assist the separation, still require approximately 15-60 minutes to determine the $pK_a$ value for one compound. The present invention offers a substantial improvement (currently up to 16 compounds per hour in a 96 capillary array) in throughput as compared to single capillary approaches. This increase in throughput is the result of using different pH buffers in different capillaries of the array to simultaneously screen the entire pH range. The different pH buffers are introduced into the different capillaries using the aforementioned vacuum assistance capabilities of the proposed invention.

Figure 5A:
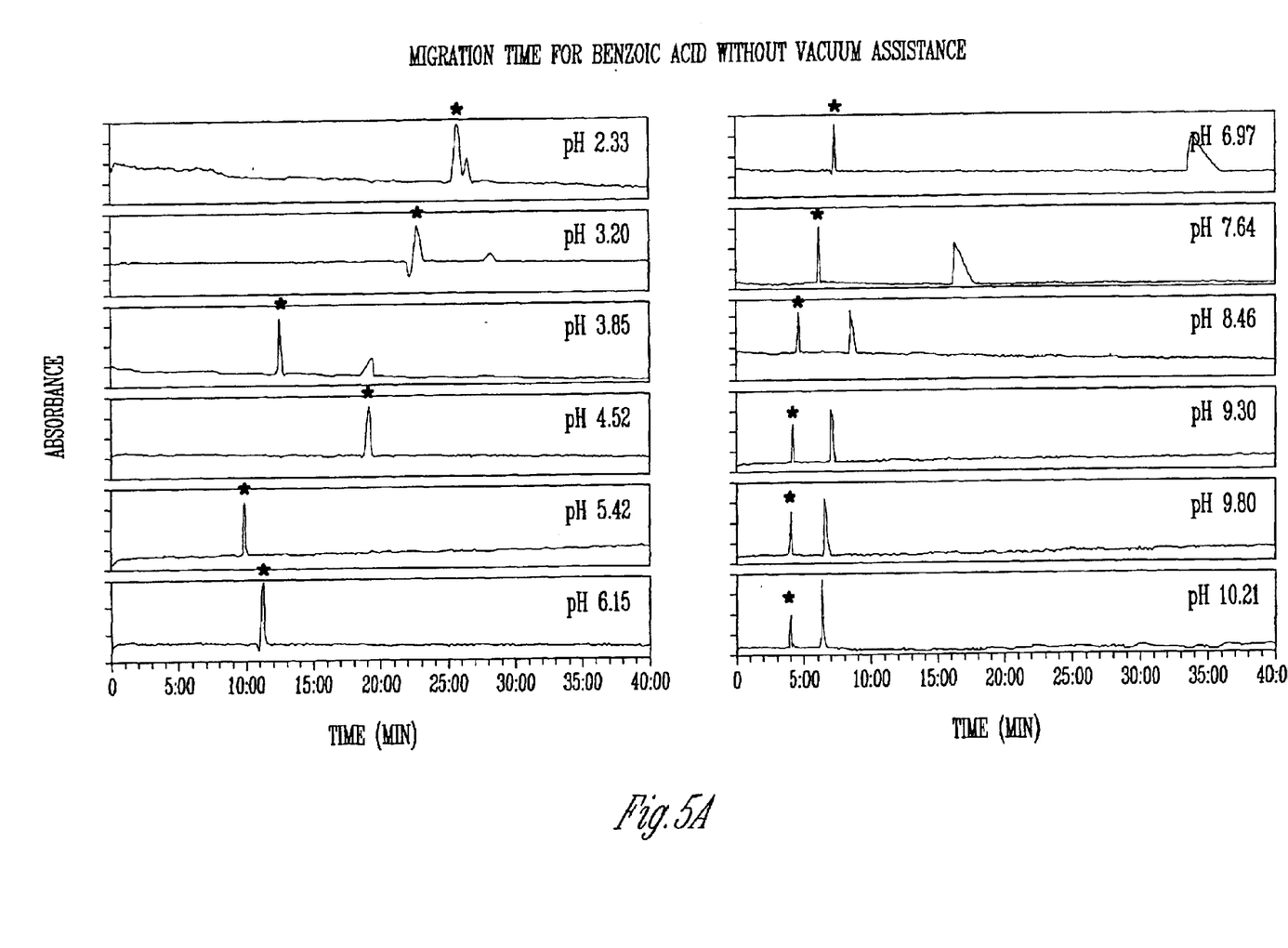
FIG. 5A presents the migration time for benzoic acid as a function of buffer pH without vacuum assistance.
Figure 5B:
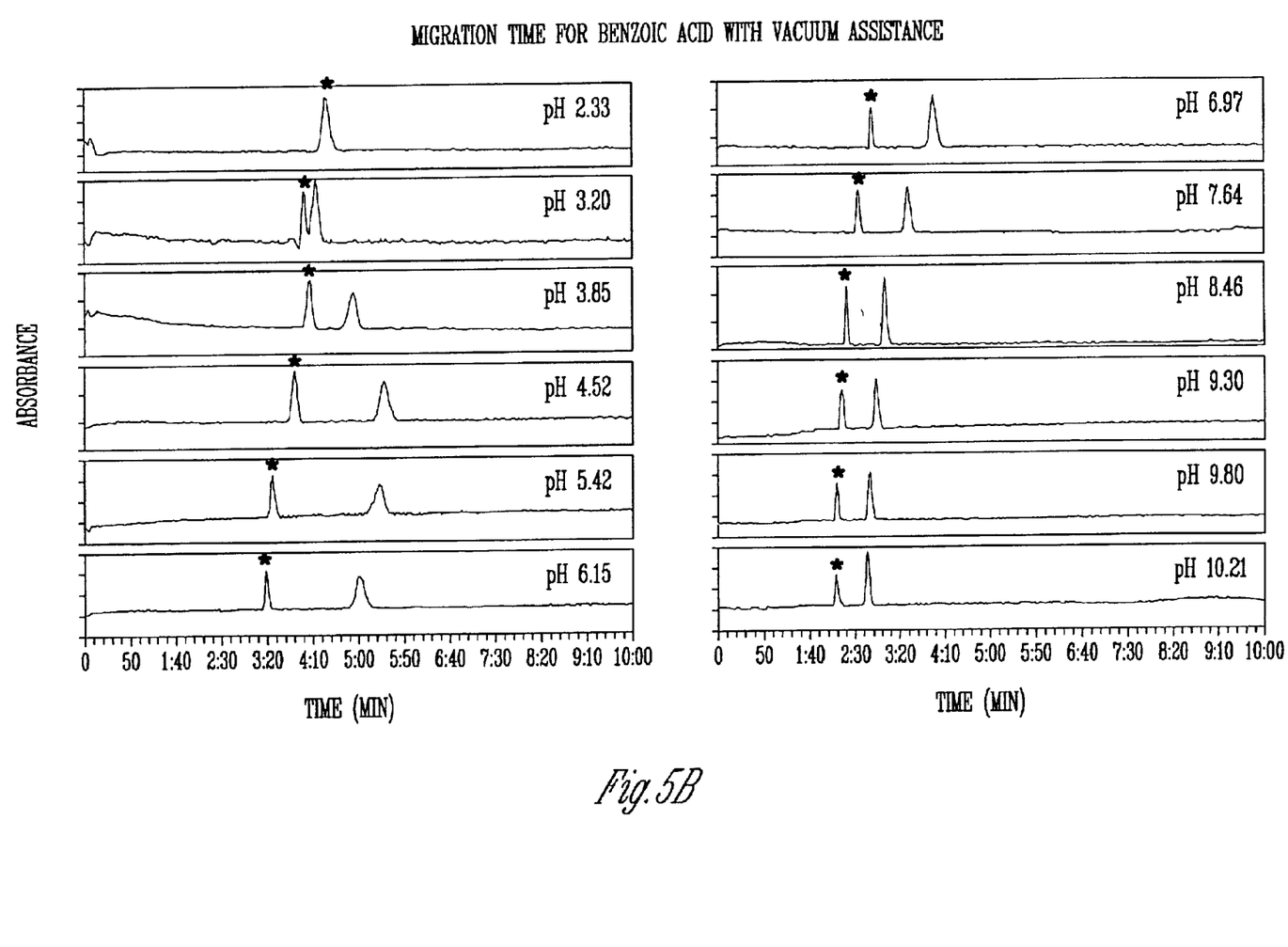
FIG. 5B presents the migration time for benzoic acid as a function of buffer pH with vacuum assistance.

FIG. 5 presents the $pK_a$ analysis of benzoic acid (literature $pK_a$ value: 4.18) obtained by using different pH buffers in different capillaries of the array. Up to eight different compounds can be interrogated at 12 different pH values using a 96-capillary array by injecting an 8×12 matrix of different buffers into the array. For both FIG. 5A and FIG. 5B, the twelve electropherograms displayed were obtained simultaneously. The sample in both FIGS. 5A and 5B consisted of a solution of 200 ppm benzoic acid in water with 0.1% (by volume) dimethylsulfoxide as a neutral marker (denoted by the asterisk). Benzoic acid is at least partially negatively charged throughout the majority of the pH range and therefore migrates after the DMSO neutral marker. Each electropherogram corresponds to a different capillary of the array that contained different running buffers ranging in pH from 2.33 to 10.21. A twelve component buffer series was utilized. All of the buffers were prepared to an ionic strength of 20 mM and comprised, in order of increasing pH, phosphate, citrate, formate, acetate, acetate, 2-(N-orpholino)ethanesulfonic acid (MES), N-(2-Acetamido)-2-aminoethanesulfonic acid (ACES), 2-[(2-Hydroxy-1,1-bis (hydroxymethyl)ethyl)amino]ethanesulfonic acid (TES), [(2-Hydroxy-1,1-bis (hydroxymethyl)ethyl)amino]-1-propanesulfonic acid (TAPS), 2-(Cyclohexylamino)ethanesulfonic acid (CHES), 3-(Cyclohexylamino)-2-hydroxy-1-(Cyclohexylamino)ethanesulfonic acid (CHES), 3-(Cyclohexylamino)-2-hydroxy-1-(Cyclohexylamino)ethanesulfonic acid (CHES), 3-(Cyclohexylamino)-2-hydroxy-1-propanesulfonic acid (CAPSO), and 3-(Cyclohexylamino)-1-propanesulfonic acid (CAPS). The capillary tubes were initially all filled with 20 mM ionic strength borate buffer at pH 9.0, following which the capillaries were filled with the different pH buffers from the inlet tray by using a vacuum of −1.0 psi for 10 minutes. The same 96-capillary array (75-μm I.D., 150-μm O.D., effective length 40 cm; total length 60 cm) was utilized for both separations. The samples were vacuum injected at −0.3 psi for 8 sec. Separations were performed at 15 kV with a running time of 40 min without vacuum assistance (FIG. 5A) and 10 min with −0.4 psi vacuum assistance (FIG. 5B).

FIG. 5A shows electropherograms obtained for a pH range from 2.3-10.2 without vacuum assistance. It is evident that the migration time for benzoic acid is prohibitively long in the intermediate pH range from pH 4-8, such that the benzoic acid is not observed in 40 min from a pH of 4.5-7. This is due to the absence of a strong EOF at lower pH values, and limits the applicability of this CE technique (no vacuum assistance) for determining acidic $pK_a$ values.

FIG. 5B shows electropherograms obtained for benzoic acid using the same experimental conditions with the addition of −0.4 psi vacuum assistance to the separation. The analysis time has been significantly reduced to roughly 5 minutes, and the $pK_a$ value for benzoic acid can be successfully determined by plotting its electrophoretic mobility as a function of pH. The inflection point of the resulting sigmoidally shaped plot corresponds to the $pK_a$ value. This demonstrates the necessity of providing vacuum assistance to the separation to successfully determine $pK_a$ values over a clinically relevant (pH 2-10) range. By placing different pH buffers in different capillaries, the throughput is substantially improved compared to single capillary, sequential approaches.

EXAMPLE 3

(Comparison of Migration Time and Peak Shape in log $P_{ow}$ Analysis With and Without Vacuum Assistance)

This example illustrates the necessity of using vacuum to assist the electrophoretic mobility in the determination of the lipophilicity of drug compounds. Relative drug lipophilicities are most often correlated to the octanol-water partition coefficient (log $P_{ow}$ value), defined as the equilibrium concentration ratio of a compound between a 1-octanol phase and an aqueous phase. Log $P_{ow}$ values are used to predict drug transport properties relationships. An increasing trend in the pharmaceutical industry has been to determine physicochemical properties of drug candidate compounds earlier in the drug development process, as such information can increase the overall success in drug discovery. Therefore, when one considers the rapid growth of drug candidate synthesis using combinatorial methods, analytical approaches to rapidly estimate physicochemical properties such as log $P_{ow}$ and $pK_a$ values are in high demand.

Figure 6A:
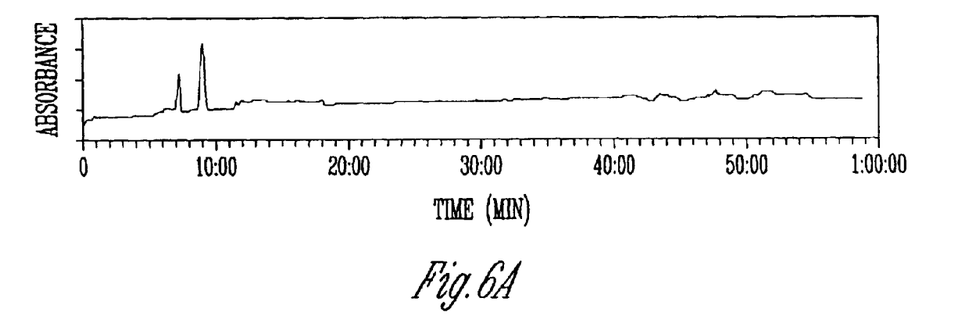
FIG. 6A presents the separation of DMSO, caffeine and dodecylbenzene without vacuum assistance.

The log $P_{ow}$ value can be estimated by measuring a drug's electrophoretic mobility in a microemulsion running buffer relative to two standard compounds. The first standard (DMSO) marks the electroosmotic flow (EOF) and the migration time of a compound that is not incorporated into the microemulsion. The terminal standard (dodecylbenzene) marks the microemulsion migration time. Use of these migration times allows one to calculate the capacity factor of a drug compound, which is converted to its log $P_{ow}$ value. FIG. 6A presents a plot of migration time versus absorbance (an electropherogram) obtained for a sample mixture containing 0.25% by volume dimethylsulfoxide (DMSO), 600 ppm caffeine and 0.08% dodecylbenzene. The peak with the lower migration time (approximately 7 minutes) is DMSO. The peak with the longer migration time (approximately 9 minutes) is caffeine. A peak corresponding to dodecylbenzene is not clearly visible. The sample was dissolved in a running buffer and introduced into a capillary tube containing a running buffer using a vacuum level of −0.2 psi for 10 seconds. The running buffer consisted of a microemulsion solution containing 8.16% 1-butanol, 1.19% n-heptane, 3.31% sodium dodecylsulfate and 87.34% 68 mM 3-(Cyclohexylamino)-1-propanesulfonic acid (pH 10.3). The relatively high current generated by the microemulsion buffer was such that a low running voltage (6 kV) was employed to minimize the effects of joule heating in the capillary array, resulting in misshapen peaks and an unacceptably long analysis time. The terminal standard, dodecylbenzene, migrates at approximately 55 minutes although it is not clearly visualized under these conditions. This may be due to the fact that the dodecylbenzene migration time is too long, leading to poor peak shape.

Figure 6B:
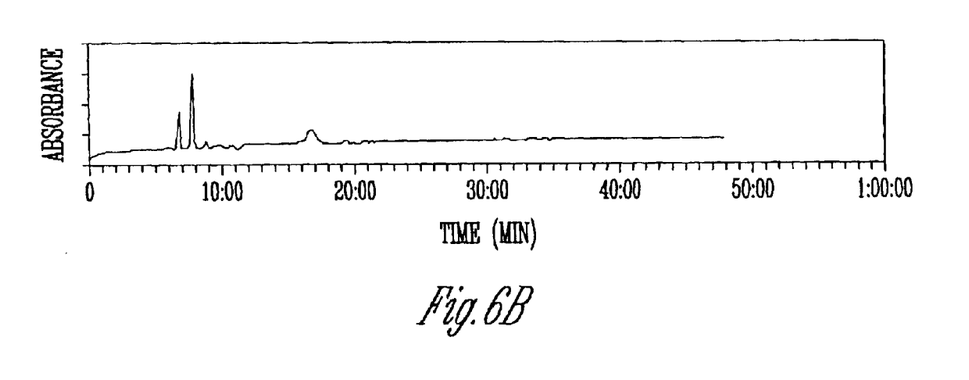
FIG. 6B presents the separation of DMSO, caffeine and dodecylbenzene with vacuum assistance.

FIG. 6B illustrates the same separation with the application of −0.05 psi vacuum to assist the separation. The peak with the lowest migration time (approximately 7 minutes) is DMSO. The middle peak (at approximately 8 minutes) is caffeine and the broader peak (at approximately 17 minutes) with the longest migration time corresponds to broader peak (at approximately 17 minutes) with the longest migration time corresponds to dodecylbenzene. The peaks are much sharper upon the addition of vacuum assistance, the baseline is less noisy than in FIG. 6A, and the terminal dodecylbenzene standard is now visible making the log $P_{ow}$ determination possible. The sharper peaks also facilitate more accurate migration time selection, improving the accuracy of the analysis. Importantly, the overall analysis time has been reduced to less than twenty minutes from one hour. As up to 96 separate compounds (in a 96 capillary array) could be simultaneously screened for their respective log $P_{ow}$ values using the described capillary array, the overall higher throughput provided by the vacuum assistance system of the invention is extremely beneficial for drug discovery.

EXAMPLE 4

(Substantial Decrease in CE Analytical Method Development Time Using the Invention)

Figure 7:
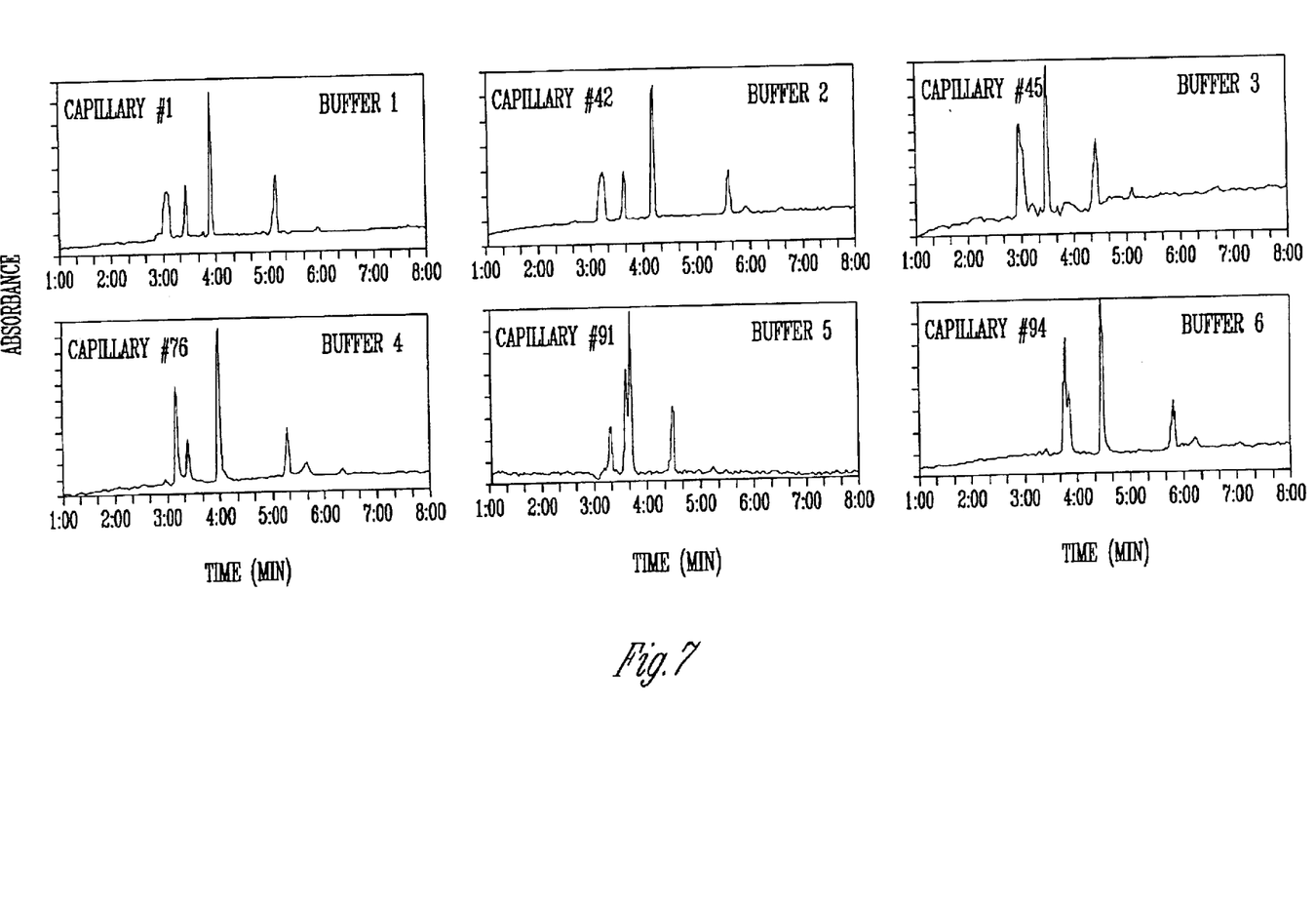
FIG. 7 presents the separation of caffeine, 4-acetamidophenol, 2-acetamidophenol and acetylsalicylic acid in different buffer solutions.

This example demonstrates the use of this invention to significantly decrease CE method development time. In CE as in most analytical techniques, it is necessary to optimize the analytical method to provide the highest possible quality of data in the shortest possible analysis time. Most often in CE, this involves the optimization of running buffer salt and additive concentrations, pH, and ionic strength. In this example, the time to evaluate which of six different possible running buffers will provide the best resolution is reduced significantly. This is possible because the system permits the operator to simultaneously examine different separation conditions in a single run. FIG. 7 demonstrates this concept in which the common, outlet reservoir contained a borate buffer while six different running buffers were loaded into 16 capillaries each of a 96-capillary array. All 96 capillary tubes were initially filled with a 50 mM borate buffer (pH 9.0) after which the six different buffers were loaded into 16 capillaries each of the array electrophoretically using a voltage of 15 kV for 15 minutes. The sample contained a mixture of caffeine, 4-acetamidophenol, 2-acetamidophenol and acetylsalicylic acid (in order of migration) at a concentration of 250 ppm each. The samples were vacuum injected at −0.3 psi for 10 seconds. The separation was performed at a voltage of 15 kV. The buffers were as follows: buffer 1 was 50 mM boric acid pH 9.0; buffer 2 was 45 mM boric acid pH 9.0, 10% methanol; buffer 3 was 25 mM boric acid pH 9.0, 25 mM SDS; buffer 4 was 25 mM boric acid pH 9.0, 25 mM SDS, 10% methanol; buffer 5 was 25 mM boric acid pH 9.0, 50 mM SDS; and buffer 6 was 25 mM boric acid pH 9.0, 50 mM SDS, 10% methanol. The separation efficiencies of the six different buffers were monitored simultaneously. It is easy to see that up to 96 different running buffers could potentially be evaluated in one run.

FIG. 7 displays the results from representative capillary tubes of a 96 capillary tube array. FIG. 7 shows that the number of runs needed to make a decision on the best running buffer was reduced from the time required to perform six separations to the time required to perform one separation. In this example, Buffer 1 was selected as the best running buffer. Buffers 3, 5, and 6 did not completely resolve the analytes. Buffers 2 and 4 contained methanol, but did not provide better performance. Overall, the time to select the best method was reduced from hours to minutes using this approach.

EXAMPLE 5

(Use of Invention to Significantly Speed the Optimization of Chiral Analysis)

This example demonstrates the use of this invention to quickly determine an optimal chiral selector to effect an enantiomeric separation. Capillary electrophoresis offers several substantial advantages when compared to traditional chiral liquid chromatography approaches that require expensive, specialized columns to perform enantiomeric separations. In CE, a single universal column can be used and various chiral selectors are added to the background electrolyte for achieving a separation. As no universal chiral resolving agent exists, most often numerous selectors must be evaluated sequentially until an optimal selector is determined. These chiral selectors can be very expensive. By minimizing the amount of selector used and the time necessary to select an optimal selector, the overall cost for chiral analysis can be significantly reduced.

In this example, a low cost running buffer consisting of 25 mM phosphoric acid, 15 mM triethylamine (pH 2.5) was placed in the common outlet reservoir and initially filled into the capillaries. Running buffers containing three different chiral selectors, α-, β-, and γ-sulfated cyclodextrin, were injected into different capillaries of the 96-capillary array using the vacuum assistance device of the invention and evaluated simultaneously. For this experiment, only 24 capillaries of the array contained selector while the other capillaries contained outlet buffer only. The separation efficiencies provided by the different chiral selectors for four different analytes, alprenol, p-chloroamphetamine, isoproterenol and metoprolol, were monitored simultaneously. The various analytes were prepared at 250 ppm concentrations and vacuum injected for 8 seconds at −0.3 psi, and a voltage of −5.5 kV was used for the analysis. The capillary dimensions used were 75-μm I.D., 150-μm O.D., 28 cm effective length, and 52 cm total length.

Table 1 summarizes the data in terms of the enantiomeric resolution ($R_s$) and overall migration time. It is evident that for each compound at least one selector provided enantiomeric resolution ($R_s$>1) in less than 25 minutes. If no peaks were observed in one hour (—), it was assumed that the interaction between the chiral selector and the analyte was too weak to impart an overall mobility to the analyte. This approach significantly reduces the time to determine which chiral selector is appropriate, eliminating the need to perform several different separation runs. By using this approach, the relative enantiomeric selectivity of many different types of selectors can be examined simultaneously at reduced cost to the analyst.

TABLE 1

| Capillary # | Sample | Sulfated Cyclodextrin Type (1.5%) | $R_s$ | Migration Time (min) |
|---|---|---|---|---|
| 2 | Alprenol | α | 1.35 | 40 |
| 6 | Alprenol | β | 1.02 | 22 |
| 10 | Alprenol | γ | 1.06 | 19 |
| 14 | Alprenol | α | Split Peak | 34 |
| 18 | Alprenol | β | 1.00 | 22 |
| 22 | Alprenol | γ | 1.01 | 17 |
| 26 | p-Chloroamphetamine | α | N/R | 16 |
| 30 | p-Chloroamphetamine | β | 1.37 | 17 |
| 34 | p-Chloroamphetamine | γ | 5.44 | 54 |
| 38 | p-Chloroamphetamine | α | N/R | 16 |
| 42 | p-Chloroamphetamine | β | 1.48 | 20 |
| 46 | p-Chloroamphetamine | γ | 4.51 | 43 |
| 50 | Isoproterenol | α | — | — |
| 54 | Isoproterenol | β | 1.75 | 19 |
| 58 | Isoproterenol | γ | — | — |
| 62 | Isoproterenol | α | — | — |
| 66 | Isoproterenol | β | 2.12 | 24 |
| 70 | Isoproterenol | γ | — | — |
| 74 | Metoprolol | α | — | — |
| 78 | Metoprolol | β | 1.02 | 13 |
| 82 | Metoprolol | γ | 2.61 | 54 |
| 86 | Metoprolol | α | — | — |
| 90 | Metoprolol | β | 1.09 | 14 |
| 94 | Metoprolol | γ | 1.89 | 47 |

From the above examples it can be seen that the invention accomplishes at least all of its stated objectives and that off-axis setting, use of vacuum, and use of a common outlet reservoir to allow simultaneous running of different buffers in test capillaries, are all improvements on the basic Yeung test system. It goes without saying that minor changes in the system and its operational methodology can be made without departing from the spirit and scope of the invention.

What is claimed is:

1. A multiplexed, absorbance-based capillary electrophoresis system for separation and analysis of multiple samples simultaneously without use of a mask or slit comprising:

a planar array of capillary tubes for containment of samples having at least one light absorbing species;

a photodetector for detecting light passing through the capillary tubes positioned on a common axis with and parallel to the planar array of capillary tubas at a distance such that the array of capillary tubes is visible and in focus, such that detection of absorbance of light by a sample in the planar array of capillary tubes indicates the presence of the absorbing species in said sample; and a light source positioned with respect to the photodetector so that a majority of light that passes between capillary tubes in the planar array of capillary tubes does not reach the photodetector.

2. The system of claim 1 wherein the photodetector is positioned at a distance which is at least about 10 times a cross-sectional distance of a capillary tube measured orthogonally to the planar array of capillary tubes.

3. The system of claim 1 wherein an area where light is emitted from the light source is positioned in an off-axis alignment.

4. The system of claim 3 wherein an offset angle is between 135° and 180°.

5. The system of claim 3 wherein the offset angle is between 160° and 180°.

6. The system of claim 1 wherein the distance is from about 3 cm to about 40 cm.

7. The system of claim 1 wherein the planar array of capillary tubes comprises at least about 10 capillary tubes.

8. The system of claim 1 wherein the planar array of capillary tubes comprises at least about 90 capillary tubes.

9. The system of claim 1 wherein the photodetector is a linear photodiode array.

10. The system of claim 1 wherein the light source emits light of a wavelength between 180 nm to about 1500 nm.

11. The system of claim 1 wherein the light source has a power output of about 0.5 mW to about 50 mW.

12. The system of claim 1 which further comprises an optical filter positioned between the planar array of capillary tubes and the photodetector.

13. The system of claim 1 which further comprises a flat-field lens positioned between said planar array of multiple capillary tubes and the photodetector.

14. The system of claim 1 which further comprises a collimating lens positioned between the light source and the planar array of capillary tubes.

15. A multiplexed, absorbance-based capillary electrophoresis system for separation and analysis of multiple samples simultaneously without use of a mask or slit comprising:

a planar array of capillary tubes having inlet ends and outlet ends for containment of samples having at least one light absorbing species;

a photodetector for detecting light passing through the capillary tubes positioned on a common axis with and parallel to the planar array of capillary tubes at a distance such that the array or capillary tubes is visible and in focus, such that detection of absorbance of light by a sample in the planar array of capillary tubes indicates the presence of the absorbing species in said sample;

a light source positioned with respect to the photodetector so that the majority of light that passes between capillary tubes in the planar array of capillary tubes does not reach the photodetector; and a vacuum source operatively connected to the outlet ends of the capillary tubes.

16. The system of claim 15 wherein the photodetector is positioned at a distance which is at least about 10 times a cross-sectional distance of a capillary tube measured orthogonally to the planar array of capillary tubes.

17. The system of claim 15 wherein an area where light is emitted from the light source is positioned in an off-axis alignment.

18. The system of claim 17 wherein an offset angle is between 135° and 180°.

19. The system of claim 17 wherein the offset angle is between 160° and 180°.

20. The system of claim 15 wherein the distance is from about 3 cm to about 40 cm.

21. The system of claim 15 wherein the planar array of capillary tubes comprises at least about 10 capillary tubes.

22. The system of claim 15 wherein the planar array of capillary tubes comprises at least about 90 capillary tubes.

23. The system of claim 15 wherein the photodetector is a linear photodiode array.

24. The system of claim 15 wherein the light source units light of a wavelength between 180 nm to about 1500 nm.

25. The system of claim 15 wherein the light source has a power output of about 0.5 mW to about 50 mW.

26. The system of claim 15 which further comprises an optical filter positioned between the planar array of capillary tubes and the photodetector.

27. The system of claim 15 which further comprises a flat-field lens positioned between said planar array of multiple capillary tubes and the photodetector.

28. The system of claim 15 which further comprises a collimating lens positioned between the light source and the planar array of capillary tubes.

29. The system of claim 15 wherein the capillary tube inlets have separate associated inlet reservoirs and the outlet end of each has a common outlet reservoir.

30. A multiplexed, absorbance-based capillary electrophoresis system for separation and analysis of multiple samples simultaneously without use of a mask or slit comprising:

a planar array of capillary tubes having inlet ends and outlet ends for containment of samples having at least one absorbing species;

a photodetector for detecting light passing through the capillary tubes positioned on a common axis with and parallel to the planar array of capillary tubes at a distance such that the array of capillary tubes is visible and in focus; such that detection of absorbance of light by a sample in the planar array of capillary tubes indicates the presence of the absorbing species in said sample;

a light source positioned such that the area where light is emitted is on-axis with the planar array of capillary tubes and the photodetector; and a vacuum source operatively connected to the outlet ends of the capillary tubes.

31. The system of claim 30 wherein the photodetector is positioned at a distance which is at least about 10 times a cross-sectional distance of a capillary tube measured orthogonally to the planar array of capillary tubes.

32. The system of claim 30 wherein the distance is from about 3 cm to about 40 cm.

33. The system of claim 30 wherein the planar array of capillary tubes comprises at least about 10 capillary tubes.

34. The system of claim 30 wherein the planar array of capillary tubes comprises at least about 90 capillary tubes.

35. The system of claim 30 wherein the photodetector is a linear photodiode array.

36. The system of claim 30 wherein the light source emits light of a wavelength between 180 nm to about 1500 nm.

37. The system of claim 30 wherein the light source has a power output of about 0.5 mW to about 50 mW.

38. The system of claim 30 which further comprises an optical filter positioned between the planar may of capillary tubes and the photodetector.

39. The system of claim 30 which further comprises a flat-field lens positioned between said planar array of multiple capillary tubes and the photodetector.

40. The system of claim 30 which further comprises a collimating lens positioned between the light source and the planar array of capillary tubes.

41. The system of claim 30 wherein the capillary tube inlets have separate associated inlet reservoirs and the outlet end of each has a common outlet reservoir.

42. A method of analyzing multiple samples simultaneously by absorbance detection comprising:

irradiating a planar array of capillary tubes filled with samples with a light source that emits at least one wavelength of light absorbed by the samples, said capillary tubes having inlet ends and outlet ends;

detecting absorbance of light with a photodetector positioned with respect to the light source such that the majority of light that passes between capillary tubes in the planar array of capillary tubes does not reach the photodetector and wherein the photodetector is positioned parallel and on common axis to the planar array of capillary tubes at a distance of at least about 10 times a cross-sectional distance of a capillary tube measured orthogonally to the planar array of multiple capillary tubes.

43. The method of claim 42 which further comprises applying a vacuum to the outlet ends of the capillary tubes to achieve more rapid separations.

44. The method of claim 42 wherein the distance is from about 3 cm to about 40 cm.

45. The method of claim 42 wherein the planar array of capillary tubes comprises at least about 10 capillary tubes.

46. The method of claim 42 wherein the planar array of capillary tubes comprises at least about 90 capillary tubes.

47. The method of claim 42 wherein the photodetector is a linear photodiode array.

48. The method of claim 42 wherein the light source emits light of a wavelength between 180 nm to about 1500 nm.

49. The method of claim 42 wherein the light source has a power output of about 0.5 mW to about 50 mW.

50. The method of claim 42 wherein the capillary tube inlets have separate associated inlet reservoirs and the outlet end of each has a common outlet reservoir.

51. A method of analyzing multiple samples simultaneously by detection comprising:

irradiating a planar array of capillary tubes filled with samples with a light source that emits at least one wavelength of light absorbed by the samples, said capillary tubes having inlet ends and outlet ends;

absorbance of light with a photodetector positioned on-axis with the planar array of capillary tubes and an area where light is emitted from the light source and parallel to the planar array of capillary tubes at a distance of at least about 10 times a cross-sectional distance of a capillary tube measured orthogonally to the planar array of multiple capillary tubes; and applying a vacuum to the outlet ends of the capillary tubes to achieve more rapid separations.

52. The method of claim 51 wherein the photodetector is positioned with resect to the light source, such that the majority of light that passes between capillary tubes in the planar array of capillary tubes does not reach the photodetector.

53. The method of claim 51 wherein the distance is from about 3 cm to about 40 cm.

54. The method of claim 51 wherein the planer array of capillary tubes comprises at least about 10 capillary tube.

55. The method of claim 51 wherein the planar array of capillary tubes comprises at least about 90 capillary tubes.

56. The method of claim 51 wherein the photodetector is a linear photodiode array.

57. The method of claim 51 wherein the light source emits light of a wavelength between 180 nm to about 1500 nm.

58. The method of claim 51 wherein the light source has a power output of about 0.5 mW to about 50 mW.

59. The method of claim 51 wherein the capillary tube inlets have separate associated inlet reservoirs and the outlet end of each has a common outlet reservoir.

* * * * *

UNITED STATES PATENT AND TRADEMARK OFFICE
CERTIFICATE OF CORRECTION

PATENT NO. : 6,833,919 B2
DATED : December 21, 2004
INVENTOR(S) : Kenseth et al.

It is certified that error appears in the above-identified patent and that said Letters Patent is hereby corrected as shown below:

Column 15,
Line 47, "tubas" should read -- tubes --

Column 16,
Line 61, "units" should read -- emits --

Column 17,
Line 48, "may" should read -- array --

Column 18,
Line 6, insert -- a -- between "on" and "common"
Line 29, insert -- absorbance -- between "by" and "detection"
Line 34, insert -- detecting -- before "absorbance"
Line 51, "tube" should read -- tubes --

Signed and Sealed this

Twenty-ninth Day of March, 2005

JON W. DUDAS
*Director of the United States Patent and Trademark Office*